United States Patent [19]

Grass et al.

[11] Patent Number: 4,578,806
[45] Date of Patent: Mar. 25, 1986

[54] DEVICE FOR ALIGNING COOPERATING X-RAY SYSTEMS

[75] Inventors: Joseph J. Grass, Brookfield; Marvin P. Glyzewski; Emanuel V. Polizzi, both of Waukesha, all of Wis.

[73] Assignee: General Electric Company, Schenectady, N.Y.

[21] Appl. No.: 561,941

[22] Filed: Dec. 15, 1983

[51] Int. Cl.⁴ .............................................. A61B 6/08
[52] U.S. Cl. .................................... 378/162; 378/205
[58] Field of Search ................. 378/162, 163, 164, 205

[56] References Cited

U.S. PATENT DOCUMENTS

| | | | |
|---|---|---|---|
| 2,581,431 | 1/1952 | Nelson | 378/205 |
| 3,374,350 | 3/1968 | Mills | 378/205 |
| 4,053,782 | 10/1977 | Grass | 378/162 |
| 4,061,924 | 12/1977 | Jacoby | 378/162 |

Primary Examiner—Craig E. Church
Attorney, Agent, or Firm—Fuller, House & Hohenfeldt

[57] ABSTRACT

The isocenters of two independent frontal and lateral viewing X-ray systems are made coincident using an X-ray permeable target frame that has congruent crosshairs defined by X-ray impermeable lines on opposite side walls. A small steel ball is located in the frame between side walls on a line running from the intersection of one set of crosshairs to the other. A television display of the X-ray image of the ball resting on the patient supporting table top with the frame leveled and of the crosshairs with the frontal system having the central ray of its X-ray beam vertical and then horizontal and with X-ray impermeable crosshairs on the image receptor permits shifting the frame until the crosshairs on it and on the receptor are coincident with the ball and the isocenter in vertical and horizontal orientations. The procedure for establishing the isocenter of the lateral system is comparable. The target frame is also mounted for rotating relative to protractors to measure and calibrate the angular orientations of the systems.

20 Claims, 21 Drawing Figures

DEVICE FOR ALIGNING COOPERATING X-RAY SYSTEMS

BACKGROUND OF THE INVENTION

This invention pertains to apparatus for aligning and calibrating two cooperating diagnostic X-ray systems.

In angiographic examinations, it is frequently necessary to obtain X-ray views of a blood vessel in two different directions simultaneously. For example, posterior-anterior (PA) and lateral X-ray views of the same vessel may be required. Apparatus for acquiring PA views of a blood vessel or any part of the anatomy is shown in U.S. Pat. No. 4,339,825. The apparatus shown in that patent is frequently referred to as a frontal imaging system (FIS).

Apparatus for obtaining lateral views is available from various X-ray equipment manufacturers. One such apparatus is described in U.S. Pat. application Ser. No. 421,603, filed Sept. 22, 1982, now U.S. Pat. No. 4,501,011, which is incorporated herein by reference. The referenced application is assigned to the assignee of this application. The referenced application discloses a so-called vascular gantry system (VGS) that includes an X-ray source and an X-ray image receptor that are angulatable synchronously with each other and capable of being aligned transversely to the frontal imaging system. The vascular gantry system is used for obtaining a lateral X-ray view simultaneously with obtaining a PA or frontal X-ray view.

A problem in obtaining simultaneous PA and lateral X-ray views is assuring that the central ray in the X-ray beam projected from the X-ray source to the image receptor in the frontal imaging system will continue to intersect the central ray of the lateral viewing system at a common point, called the isocenter, for all angular orientations of both systems. Accurate alignment of the vascular gantry system is difficult because it is comprised of two separate mechanisms that may be uncoupled from each other. Since all vascular examination procedures do not require lateral X-ray views, it is desirable to have a vascular gantry- system that can be easily separated from and restored to the vicinity of the patient undergoing examination in a frontal imaging system. However, when the two systems are brought into cooperating relation, it is important that alignment of the systems is assured without requiring any effort or thought by the system operator or technician.

As indicated, the two systems are aligned when their isocenters are coincident and remain coincident at all angles. The isocenter is more specifically defined as a point on the central X-ray of an X-ray beam extending from the focal spot of the X-ray tube to the center of an X-ray image receptor, such as an image intensifier, which point is intercepted by the horizontal and vertical axes about which the tube and receptor orbit or angulate jointly about the patient being examined. The patient is desirably supported in a position such that the common isocenter of both of the two systems lies on the plane in the patient containing the organ or blood vessel that is the subject of lateral and frontal X-ray views. If the isocenters do not coincide, the X-ray image produced by one system will be shifted spatialy relative to the other. In other words, each system will view a slightly different part of the region of interest in the anatomy. It is important that the isocenters of the two systems remain coincident for any angulation of the two pairs of X-ray sources and image receptors.

SUMMARY OF THE INVENTION

An objective of the present invention is to provide a device for aligning and establishing and maintaining the isocenters of a lateral and a frontal X-ray imaging system in coincidence.

The device is called an angleometer. It comprises an X-ray transparent base plate that is set on the patient supporting X-ray transmissive table at an appropriate place when the alignment procedure is in progress. An X-ray transmissive box is mounted to the top of the plate in a fashion that permits the box to rotate about a vertical axis. The box is comprised of parallel front and rear walls that are spanned by top and bottom plates. The sides of the box are open. A frame, called a target, comprised of X-ray transmissive material is mounted in the box for tilting about a horizontal axis that is perpendicular to the front and rear walls and perpendicular to a longituginal axis of the patient supporting table. Since the box is rotatable about a vertical axis on its base plate, the target frame can be considered to be rotatable about the vertical axis. X-ray impermeable lines, similar to cross-hairs, are inscribed or affixed to the sides of the target frame that face the open sides of the box. During the alignment procedure, the X-ray impervious cross-hairs or lines are presented laterally or faced in the lateral direction relative to the longitudinal axis of the table top. The frame has a central rib extending from one end wall of the frame to the other coincident with the tilting axis of the frame. There is an X-ray impervious ball fixed centrally of this rib. The ball lies on a line running from the point of intersection of the vertical and horizontal crosshairs on one side of the frame to the point of intersection of the crosshairs on the other side of the frame. Thus, if the frame is tilted on its axis, the ball should remain in a fixed position.

As a first step in the alignment procedure of the frontal imaging system, the angleometer is placed on the patient support table so that the ball is in the approximate location of the isocenter. Then with the X-ray tube or source and image receptor in vertical alignment, an X-ray exposure is made. Previously, X-ray impervious crosshairs are assumed to have been applied for temporary use to the input face of the X-ray image receptor which is typically an X-ray image intensifier. The position of the ball relative to the point of intersection of the crosshairs on the image receptor input face is displayed on the screen of a television monitor. The patient support table top is then moved laterally and longitudinally to position the ball at the intersection of the crosshairs on the input face, which intersection lies on a line passing vertically through the isocenter. The frontal imaging system U-arm is now rotated to the horizontal position with the X-ray beam projected along line X-X, FIG. 1.

During an X-ray exposure, the position of the ball relative to the point of intersection of the crosshairs on the image receptor input face is displayed on the screen of a television monitor. The patient support table is then moved vertically to position the ball at the intersection of the crosshairs on the input face, which intersection lies on a line passing horizontally through the isocenter. The ball in the angleometer is now positioned precisely at the frontal system isocenter.

Now to align the lateral or vascular gantry system with the frontal imaging system, the X-ray tube of the vascular gantry system is leveled to project its central ray horizontally and an X-ray exposure is made for displaying the X-ray impervious crosshairs or lines of the frame on the lateral/television screen. If the displayed image reveals that the angleometer horizontal X-ray impervious lines on opposite sides of the target frame do not coincide, the X-ray tube is adjusted vertically. If the vertical lines of the crosshairs on opposite sides of the target frame do not coincide, the vascular gantry system is adjusted horizontally. With the X-ray source aligned so that its central horizontal ray of the X-ray beam passes through the angleometer ball, the horizontal and vertical crosshairs on both sides of the target are congruent or coincide. A substantially similar procedure is followed to align the X-ray image receptor so that the image of the angleometer ball and X-ray impervious crosshairs fall on the center of the image intensifier screen of the vascular gantry system.

Use of the angleometer insures that the central ray of the lateral X-ray beam passes through the isocenter of the frontal imaging system X-ray beam when the vascular gantry system is positioned with its X-ray source and image receptor in any combination of horizontal and vertical angles within its range. The angleometer target frame is tiltable about axes parallel to the longitudinal axis with which the patient would be coincident and also about a vertical axis. At every angle of rotation within its range, the target X-ray impervious cross strips coincide, as viewed by the television system, if the central ray of the lateral radiation field is perfectly aligned with the rotated target, whether the lateral radiation field rotation is about a horizontal or vertical axis or both.

The angleometer also facilitates calibrating the vascular gantry system at initial installation for automatic or semi-automatic operation. In the preferred construction, a protractor is employed to measure the amount of rotation of the target frame about each axis. Preferably the target frame and vascular gantry system are initially tilted about the horizontal axis to the maximum angle on one side of the central position and then tilted in two directions about the vertical axis. The coordinate positions of the vascular gantry system at the three angular positions and central position are used to calibrate a microprocessor control system. The control system is programmed to interpolate all intermediate angles for rapid and efficient and automatic control of the vascular gantry system about both horizontal and vertical axes. A more detailed description of the construction of the angleometer device and the method of its use will now be set forth in reference to the drawings.

DESCRIPTION OF THE DRAWINGS

FIG. 16, composed of parts A, B and C, are partial views of the angleometer image showing the sequence of steps for finally aligning the X-ray source to the frontal imaging system isocenter; and FIG. 17, composed of parts A, B and C, are views of the angleometer and X-ray image receptor input face showing the sequence of steps for finally aligning the X-ray image intensifier or receptor to the frontal imaging system isocenter.

DESCRIPTION OF A PREFERRED EMBODIMENT

Figure 1:
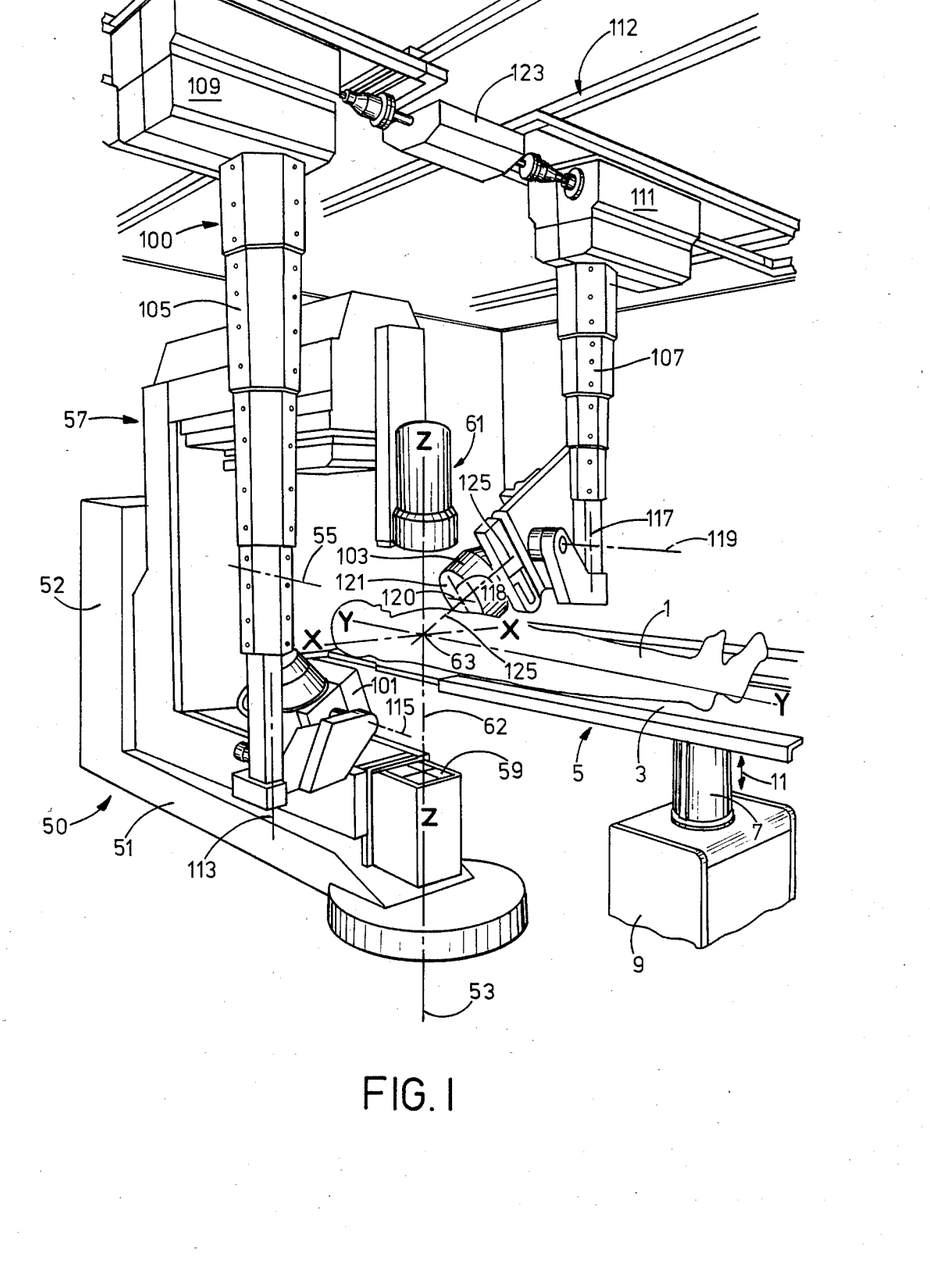
FIG. 1 is a perspective view of two typical X-ray imaging systems which can be aligned or have their isocenters established in coincidence with the new angleometer.

FIG. 1 shows a frontal X-ray imaging system and what is called a vascular gantry system or, more generally, a lateral viewing X-ray system arranged for cooperating with each other. Use of the new angleometer for aligning the two systems will be described in detail later. In FIG. 1, the body of a patient 1 is shown in outline supported on a vertically adjustable X-ray transmissive table top 3. The longitudinal axis of the patient is designated the Y axis of the system. The X axis is a horizontal axis perpendicular to the Y axis. The Z axis is a vertical axis intersecting the horizontal X and Y axes. The intersection point 63 of the three axes coincides with the common isocenter of the systems. During an X-ray examination procedure, the anatomy of interest, a blood vessel for example, should be at the isocenter or intersection of the X, Y and Z axes.

The patient supporting X-ray transmissive table top 3 is supported on a frame 5 that is mounted in cantilever fashion on a column 7 which extends from a floor mounted housing 9. The housing contains mechanism, not visible, for raising and lowering column 7 and, hence, the frame 5 that supports the table top 3. The motion of column 7 is indicated by the arrowheaded line marked 11. X-ray transmissive table top 3 in FIG. 1 is mounted on the frame 5 in such manner that the table top can be shifted bidirectionally in the X and Y directions, although the hardware for enabling the table top to be shifted is not illustrated.

The frontal imaging system comprises an L-shaped arm generally indicated by numeral 50 that has a horizontal leg 51 and a vertical leg 52. A bearing in the floor, not shown, permits the L-shaped arm, hereafter called the L-arm, to swing in a horizontal plane about a vertical or Z axis 53.

The frontal X-ray system also includes a U-shaped (U-arm) 57 that is -mounte-d to the vertical leg 52 of the L-arm for rotation about a horizontal axis 55. The shaft supporting the U-arm for rotating on the L-arm is not visible. Vertical axis 53 and horizontal axis 55 intersect at the isocenter pornt 63. An image of that point on the frontal imaging system television display screen remains fixed for all combinations of angular positions of the U-arm 57 relative to the L-arm 50.

A casing 59 containing an X-ray tube, not visible, is mounted to the outer end of the lower leg 51 of the U-arm. Assume that the Z axis or axis 53 passes through focal spot on the X-ray tube target such that the central ray 62 emergent from the X-ray tube is coincident with the Z axis. The upper leg of the U-arm 57 has an image receptor in the form of an X-ray image intensifier 61 mounted to it. The central ray of the X-ray beam passes through the lower image input face of the image intensifier and centrally thereof. When the U-arm is vertically oriented, central ray line 62, vertical axis 53 and the Z axis coincide. By swinging the L-arm 51 and 52 about the vertical axis 53, horizontal axis 55 may be made coincident to either the X or Y axes or at any angle between them. A frontal imaging system of the type just outlined, is described in greater detail in U.S. Pat. No. 4,339,825, which is assigned to the assignee of this application and is incorporated herein by reference.

The other lateral viewing X-ray imaging system, herein called "a vascular gantry system" comprises an X-ray source 101 and an opposite X-ray image receptor in the form of an X-ray intensifier 103. The X-ray source 101 is mounted to a vertically telescoping hanger 105 which is well known to those familiar with the X-ray apparatus art and need not be described in detail. The image intensifier 103 is mounted to the lower end of a telescoping hanger 107. The hanger 105 for X-ray source 101 is supported from a carriage 109 and the hanger 107 for the image intensifier 103 is supported from a carriage 111. The X-ray source is mounted to the arm to have two angular degrees of freedom. The source can rotate about a vertical axis 113 and about a horizontal axis 115. Similarly, X-ray image intensifier 103 can rotate about a vertical axis 117 and a horizontal axis 119. To provide for moving the X-ray source 101 and X-ray image intensifier 103 jointly longitudinally along the patient or along the Y axis, the carriages 109 and 111 are mounted on tracks 112. The X-ray source 101 and intensifier 103 are mounted to the telescoping hangers 100 and 107 in a fashion that permits them to be moved or adjusted toward and away from each other or generally in the X direction. The vascular gantry system is described in greater detail in the previously mentioned co-pending patent application, having U.S. Ser. No. 421,603.

DESCRIPTION OF THE ANGLEOMETER

Figure 2:
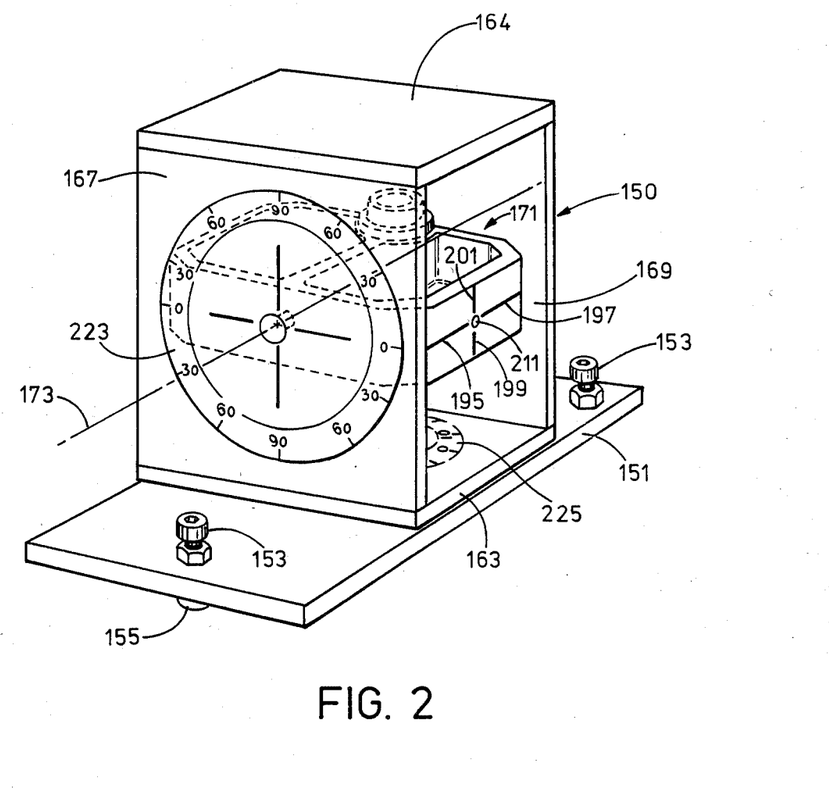
FIG. 2 is a perspective view of the angleometer.

The new multiple system aligning device or angleometer is designated generally by the numeral 150 and is illustrated in FIGS. 2-5. Referring to FIG. 2, the angleometer comprises a base plate 151 composed of an X-ray and light transmissive material such as an acrylic resin which may be one known by the trademarks "Plexiglass" or "Lucite". Three screws 153 are threaded into base plate 151 for leveling the base plate relative to a horizontal plane when the base plate is mounted on the X-ray table top. The leveling screws have rubber boots 155 fitted onto their lower ends to provide friction so the angleometer will not slip easily on the surface of the X-ray table top.

Figure 4:
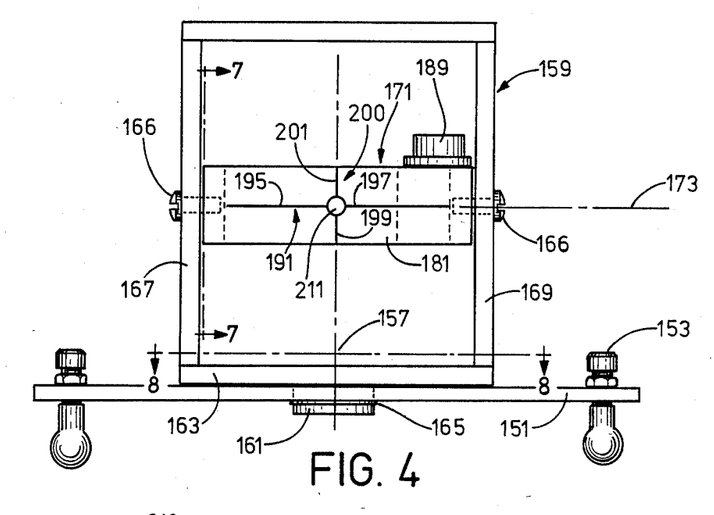
FIG. 4 is a side elevation view of the angleometer.

Still referring to FIG. 2, a housing constructed with plates of an X-ray and light transmissive material is mounted on base plate 151. The housing, hereafter called a box for the sake of brevity, has a front wall 167 and a rear wall 169 spaced apart and arranged in parallelism with each other. The front and rear walls are target assembly support members and are fastened, such as with an adhesive, to a planar bottom plate member 163 and a top or cover plate member 164 also spans between and is fastened to front and rear walls 167 and 169. The planes of the upstanding or vertical front and rear walls are perpendicular to the plane of the bottom plate member. The box in FIG. 2 is rotatable about a vertical axis or an axis that is perpendicular to the plane of base plate 151. As shown in FIG. 4, for enabling rotation, a tubular element or shaft 161 comprised of acrylic resin is adhered to the bottom plate 163 of the box. An 0-ring 165 fitted into an annular groove in shaft 161 retains the rotatable tubular shaft and, hence, the bottom plate 163 of the box in the base plate 151. Note that the sides of the box are open.

Figure 3:
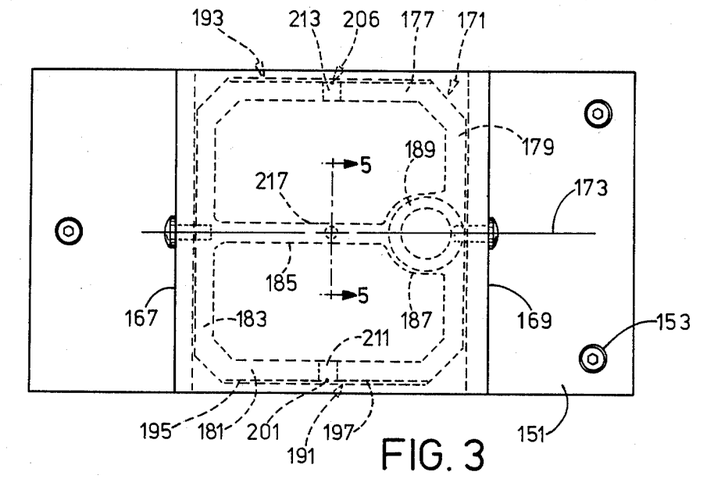
FIG. 3 is a plan view of the angleometer.

A target assembly or frame 171 is mounted for tilting within the angleometer box. A plan view of the target frame can be seen particularly well in FIG. 3 where it is shown in dashed lines. It is essentially a hollow frame defined by four outside walls 177, 179, 181 and 183. There is a rib or center wall 185 spanning between front and rear walls 183 and 179, respectively. As can be seen in FIGS. 3 and 4, the frame 171 is mounted for tilting or pivoting about a horizontal axis on a pair of coaxial screws 166 whose shanks are partially threaded for screwing into a threaded hole in front and rear walls 167 and 169 and whose tips are smooth to permit tilting without abrasion. The whole target assembly is desirably molded in a single piece out of an X-ray and light transmissive material such as acrylic resin. Screws 166 define the pivot axis 173 for the target frame 171. The central wall 185 in the frame 171 is enlarged where it joins rear wall 179 and the enlarged portion has a circular recess 187. A bubble level 189 is secured in the recess. The bubble in the level will be centered in a circular fluid-filled cavity when target frame 171 is level or perfectly horizontal.

Figures 6, 8:
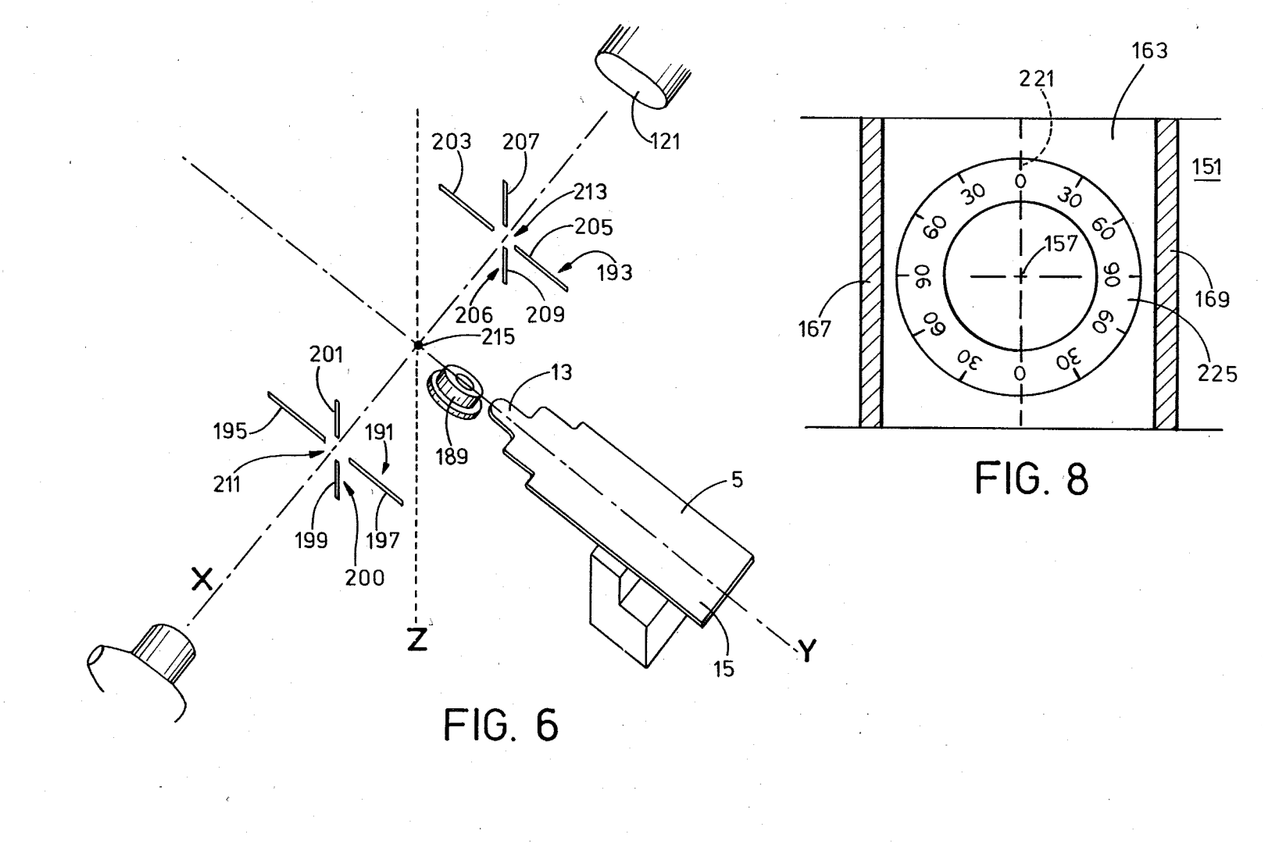
FIG. 6 is an exploded perspective and diagrammatic view of the X-ray impermeable parts of the angleometer shown in relation to the frontal image system isocenter and the vascular gantry system lateral radiation field.
FIG. 8 is a transverse sectional view taken along lines 8—8 in FIG. 4.

As shown in FIG. 4, target wall 181 has a horizontal and a vertical line 191 and 200, respectively, inscribed on it. Horizontal line 191 is comprised of 2 segments 195 and 197. Vertical line 200 is comprised of 2 segments 199 and 201. These lines are essentially crosshairs that are defined by an X-ray impervious material such as barium sulphate or fine wires such as copper or solder metal. The lines may be made by cutting or molding vertical and horizontal grooves in the outside of the wall and filling them with barium sulphate paste or a fine wire may be set in the grooves with adhesive. The horizontal X-ray impervious line 191 is perpendicular to vertical line 200. Where the lines intersect there is a hole 211 through the wall 181 of the target frame. Hole 211 is clear of X-ray impermeable line material so the central ray of an X-ray beam can pass through for reasons to be described. These X-ray impermeable lines are also shown in the FIG. 6 diagram. The rear wall 177 of target assembly 171 also has X-ray impermeable horizontal and vertical crosshair lines inscribed in it. The horizontal line is generally designated by the numeral 193 and the vertical line is generally designated by the numeral 206. As can be seen in FIG. 6, the horizontal line 193 sections are separately identified by the numerals 203 and 205 and the vertical line 206 sections are separately designated by the numerals 207 and 209. As indicated in FIG. 3, where horizontal and vertical lines 193 and 206 intersect, there is a hole through wall 177 of the target frame for the central ray of an X-ray beam to pass through. Both horizontal lines 191 and 193 lie in the same plane which also contains horizontal frame tilting axis 173, and is evident in FIGS. 3 and 4. Vertical lines 200 and 206 lie in a plane that also contains the vertical rotational axis 157 of the angleometer box, as is evident in FIG. 4. The nominal intersection point for the pairs of horizontal and vertical lines is at the center of holes 211 and 213 which are thus clear of X-ray impermeable line inscribing material. By way of illustration and not limitation, in an actual embodiment holes 211 and 213 have a 0.25 inch diameter. The horizontal and vertical X-ray impermeable lines have a width of about 0.03 inch and can have round, square or V-shaped cross-sections.

Figure 5:
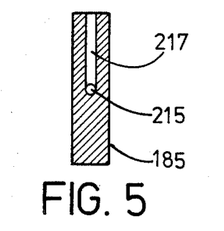
FIG. 5 is a vertical section taken along the lines 5—5 in FIG. 3.

At the intersection of the angleometer horizontal axis 173 and vertical axis 157, there is a small X-ray impervious element such as a metal ball 215 set in central target frame wall 185. The ball is shown in FIG. 5 where it is evident that it is dropped in a hole 217 that is filled with a plastic material to prevent the ball from moving. Since the ball is at the intersection of horizontal and vertical axes 173 and 157, rotation of the target about either axis does not result in displacement of the ball. By way of example and not limitation, the diameter of ball 215 in an actual embodiment is about 0.06 inches. The ball is aligned with holes 211 and 213 in the target frame.

Figure 7:
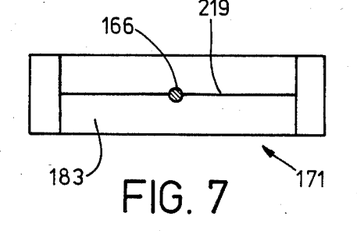
FIG. 7 is a sectional view taken along lines 7—7 of FIG. 4.
Figure 9:
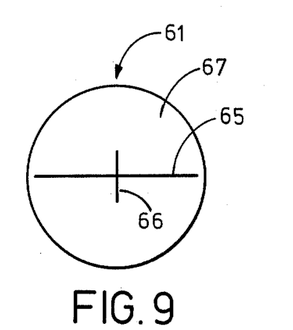
FIG. 9 is a view of the frontal imaging system X-ray image receptor image input face on which X-ray impervious crosshairs are attached.

There is a light-opaque reference line 219 inscribed on the outside of target frame wall 183, as illustrated in FIG. 7. Opaque line 219 lies in the same plane as X-ray impermeable horizontal lines 191 and 193 on the frame and, thus, line 219 intersects the common axis 173 of screws 166. Reference line 219 may be created by cutting or molding a shallow groove in the target frame wall 183 and filling the groove with black paint. In an actual embodiment, by way of example and not limitation, line 219 has a width of 0.015 inch. Reference line 219 is useful for determining the angle of tilt of the target frame. To permit measuring the horizontal tilt angle of the target frame 171 about axis 173, a protractor circle 223 is etched or otherwise inscribed on front wall 167 of the angleometer box as shown in FIG. 2. The center of the protractor circle coincides with tilt axis 173. When target frame 171 is level, reference line 219 on the target aligns with or is coincident with the zero angle line of the protractor. Reference line 219 is, of course, visible through wall 167 since the latter is transparent.

A reference line 221 is also inscribed on the top of base plate 151 as shown in FIG. 8. A protractor circle 225 is inscribed on bottom plate member 163 of the angleometer box. The center of the protractor circle 225 coincides with vertical rotational axis 157. The box 159 is at zero position about vertical axis 157 when the front and rear walls 169 are perpendicular to the long dimension of base plate 151.

Now that the construction of the angleometer has been described, its use can be explained.

Aligning the Angleometer to the Frontal Imaging System

Figure 10:
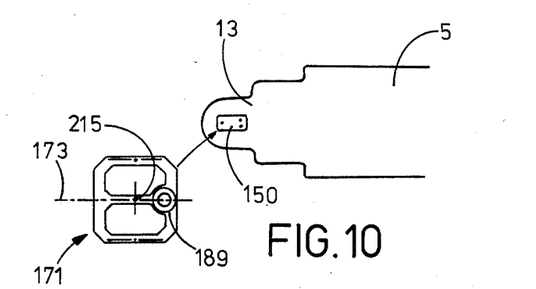
FIG. 10 is a diagrammatic representation of the placement of the angleometer on the patient support table for executing the alignment and calibration procedures.

The first thing to do is place the angleometer on the head end 13 of the patient supporting table top 3 as shown diagrammatically in FIG. 10. The target frame is adjusted to an untilted attitude, that is, its horizontal reference line 219 shown in FIG. 7 is adjusted until it coincides with the zero angle on protractor 223. The bottom protractor is used to set the box at zero rotational angle about vertical axis 157 by sighting the zero mark on the protractor and reference line 221 as shown in FIG. 8. The horizontal and vertical angles of the target frame are set while the angleometer is in place on the patient supporting table top. The angleometer is located where, by first approximation, the X-ray impervious ball 215 will be penetrated by the central ray of the frontal X-ray system beam when the L-arm 50 and U-arm 57 of the frontal X-ray system are in vertical alignment. The next step is to adjust the leveling screws 153 in the base plate of the angleometer until the bubble in the bubble level 189 is centered, thus indicating that the whole angleometer assembly is level. Prior to taking these steps, solder rods or some other X-ray impervious wires 65 and 66 are bonded to the image input face of image intensifier 61 orthogonally to each other to serve as crosshairs. Their intersection point should be coincident with the center of the image input face of the intensifier. L-arm 51 in FIG. 1 is rotated about vertical axis 53 so that the horizontal axis 55 of the U-arm 57 is parallel to the Y axis as shown in FIG. 1. U-arm 57 is set at a vertical position by using a level, not shown, so that the central X-ray from the X-ray beam source 59 is parallel to the Z axis. Now the objective is to position the ball 215 at the isocenter 63 of the frontal imaging system. When the ball is located at the isocenter, the central X-ray beam from source 59 always strikes the ball regardless of the angular location of the L-arm and U-arm about their respective axes 53 and 55.

Figure 11:
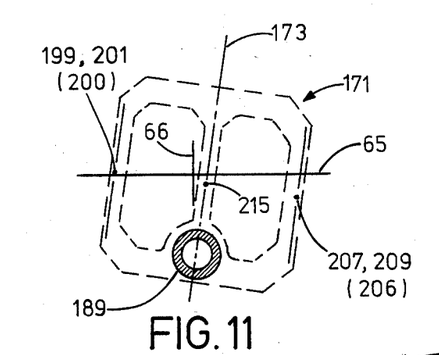
FIG. 11 is a diagrammatic representation of a television image of the angleometer as initially placed at a point which is estimated to be intersected by the central ray of the frontal imaging system.
Figure 12:
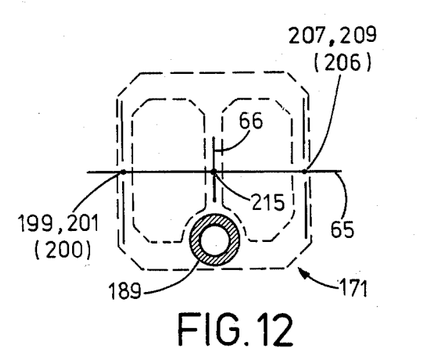
FIG. 12 is a diagrammatic representation of a plan view of the angleometer when correctly aligned horizontally with the isocenter of the frontal imaging system.

With the ball at the approximated isocenter, an X-ray exposure is made and the image formed in the X-ray image intensifier type of receptor 61 is displayed on a television monitor, not shown, but invariably associated with imaging systems of the type here under discussion. The displayed image reveals the alignment of the target assembly with respect to X-ray impermeable lines 65 and 66 on the image intensifier image input face. There may be initial misalignment as suggested in FIG. 11 where the ball 215 is displaced from the intersection of intensifier face crosshairs 65 and 66. The thing to do then is move the X-ray table top 3 in a horizontal plane only sufficiently to estimate that the position error of the ball is corrected. One or more additional X-ray exposures and horizontal shifting operations may be required to get the ball 215 coincident with the intersection point of X-ray impermeable crosshair lines 65 and 66. When there is coincidence, having the ball on the central ray of the X-ray beam is indicated. However, the target frame may still be askew relative to the reference lines 65 and 66 as is the case in FIG. 11. The angleometer base plate 151 is then moved or turned on the table top to improve the alignment of the rotational axis 173 of the target frame with the line 66 on the intensifier image input face. The vertical lines 200 and 206 on the sides of the target frame are X-ray impermeable and appear as dots on the television screen. The dots are indicated by the numerals 199, 201, 207 and 209 in FIG. 11. By turning the whole base around a vertical axis, these dots can be made to fall on the image intensifier face line 65 and, if ball 215 appears at the intersection of lines 65 and 66 on the television screens as in FIG. 12, there is assurance that the ball 215 is located along the vertical central ray of X-ray beam 62 from tube 59 and the ball is also on vertical axis or Z axis 53 of the frontal X-ray system.

It may be noted, that instead of turning the whole base of the angleometer to get the dots coincident with line 65, and angleometer box could be turned on its vertical rotational axis 157. However, this makes the protractor 225 for measuring the angle of rotation of the box depart from zero and makes another step in the calibration procedure, which is to be discussed later, a little less convenient than it could be.

The next step in the isocenter alignment procedure is to assure that the ball 215 lies on the horizontal U-arm rotational axis 55, that is, the Y axis of the U-arm 57.

Figure 13:
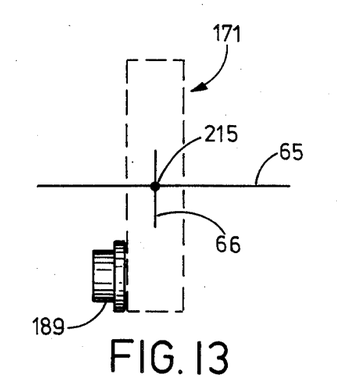
FIG. 13 is a diagrammatic representation of a lateral view of the angleometer when correctly aligned at the frontal imaging isocenter.

From the preceding operations, the ball could be above or below the intersection of the X, Y and Z axes, that is, above or below the isocenter. So the next step in the alignment procedure is to rotate the U-arm 57 90° from the position in which it is shown in FIG. 1, that is, to a horizontal attitude by using a common level, not shown, on the U-arm. Now, an X-ray exposure is made and the result viewed on the television monitor. At this time the horizontal X-ray impervious lines 191 and 193 on the sides of the target frame could be coincident and projected on the television screen as a single line. This line may be parallel to the projection on the television screen of the image intensifier input face line 66. This would indicate that the ball is above or below the X axis. The ball may not even be clearly visible as a result of it lying behind vertical X-ray impermeable lines 200 and 206 at this time. The goal is to have the central ray of the laterally directed X-ray beam pass clearly through aligned holes 211-213 in the target frame in which case the ball will be centered in the holes or the gaps created between the sections of the vertical or horizontal X-ray impermeable lines. Thus, the thing to do is raise or lower the X-ray table top and, hence, the ball until it is centered in the holes when displayed on the television screen at which time coincident lines 191 and 193 will be coincident with line 66 as in FIG. 13.

The ball 15 of the angleometer 150 is now located at the isocenter 63 of the frontal imaging system 50. The central ray 62 of the X-ray beam from X-ray source 59 will always strike the ball for every combination of angular relationships between L-arm 51 and U-arm 57. Now, the angleometer should not be touched nor should the elevation above the X-ray permeable table top 3 be changed so that alignment of the vascular gantry system can proceed.

Alignment of the Vascular Gantry System X-ray Source to the Angleometer

Figures 14, 15:
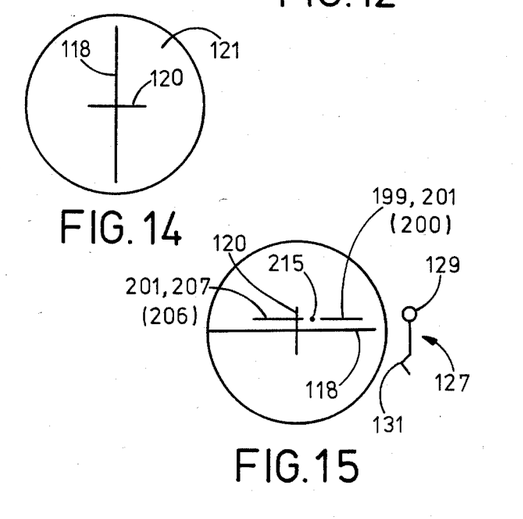
FIG. 14 is a view of the vascular gantry X-ray system image intensifier or receptor image input face with aligning X-ray impervious crosshairs attached thereto.
FIG. 15 is a partial view of the displayed angleometer image when the X-ray source is roughly aligned.

The first step is to return the U-arm 57 of the frontal X-ray system to its vertical position as shown in FIG. 1. A pair of straight and perpendicular X-ray impermeable cross lines 118 and 120 are attached to the input face of the vascular gantry system X-ray image intensifier 103 as shown in FIGS. 1 and 14. The vascular gantry system carriages 109 and 111 are coupled by means of a coupling device 123 which not only couples the carriages but provides for some synchronous driving operations of the telescoping hangers 107. The functions of the coupling device 123 are described in previously mentioned copending patent application, U.S. Ser. No. 421,603. Now the X-ray source 101 of the vascular gantry system and its X-ray image intensifier 103 are linked so that when properly aligned they will always be opposite each other and aimed at the isocenter 63 whether the source 101 and intensifier 103 are aligned in a horizontal attitude or in a mutually angulated attitude.

The vascular gantry system X-ray source 101 and X-ray image intensifier 103 are positioned so that the central ray 125 of the X-ray beam indicated in FIG. 1 passes approximately horizontally in the vicinity of the angleometer ball 215. An approximately aligned location of the X-ray source 101 is found by rotating the X-ray source 101 about vertical axis 113 and simultaneously translating carriage 109 along track system 112 until, as viewed on the television screen, the X-ray impermeable vertical line 200, composed of sections 199 and 201, on the target assembly 171 coincides with the vertical X-ray impermeable line 206, composed of sections 207 and 209, on the opposite side of the target frame, respectively, as shown in FIG. 15. The same condition exists in FIG. 6 where the vertical lines collectively designated 200 and 206 are coincident with each other. At this time in the procedure, it is not necessary that the image of the angleometer target X-ray impervious lines be in the center of the X-ray image intensifier input face cross lines 117 and 119. To facilitate further description of the procedure, FIG. 15 is provided to indicate taking a lateral view of a patient. Reference numeral 129 indicates the patient's head, and numeral 131 represents the patient's bent knees, thus indicating the upward direction. For clarity, images of the target assembly horizontal X-ray impermeable lines 191 and 193 on the side walls of the target are omitted from FIG. 15.

Next, the X-ray source 101 is manually rotated on hanger 100 about vertical axis 113 in FIG. 1 through mechanical alignment devices incorporated into the carriage 109 so that the central ray of X-ray beam 125 emanating from X-ray source 101 lies in a plane perpendicular to the Y axis in FIG. 1. The X-ray source 101 is next manually rotated about its longitudinal axis 115 so that the central ray 125 of the X-ray beam is horizontal. After each of the preceeding rotational steps, the part that is rotated is locked.

Figure 16A:
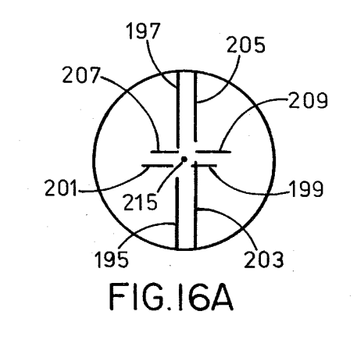
Figure 16B:
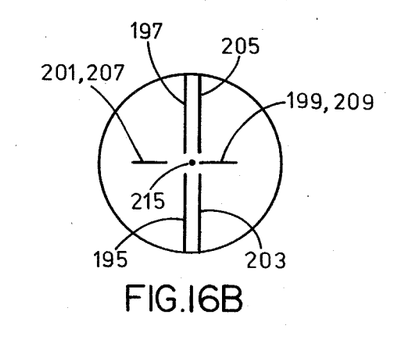
Figure 16C:
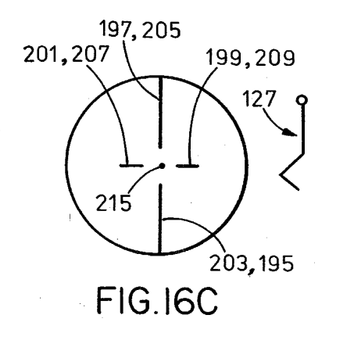

For achieving the final alignment, an X-ray exposure and a television display of the horizontal X-ray impermeable lines 191 and 193 on the target frame of the angleometer is taken. At this time lines 191 and 193 may not coincide as illustrated in FIG. 16A. In FIG. 16 the crossed X-ray impervious lines 117 and 119 that are attached to the input face of X-ray image intensifier 103 are omitted for the sake of avoiding confusion. To align the vertical X-ray impervious lines 206, composed of segments 207 and 209, with the vertical lines 200, composed of sections 201 and 199, respectively, as exhibited in FIG. 6, for example, a mechanical adjustment is made to the coupling between the X-ray source 101 and its hanger 105. The adjustment is in a direction parallel to the Y axis. When the vertical X-ray impermeable line 200 coincides with its counterpart 206, the adjustment is locked. When properly aligned in the patient head-to-foot direction, an image similar to FIG. 16(B) appears on the television screen. To align the horizontal X-ray impermeable lines 191 and 193 as exhibited in FIG. 6, a second mechanical correction is made in the height of the X-ray source 101. When the X-ray source is properly aligned vertically, the image resulting from an X-ray exposure of the angleometer will appear as in FIG. 16(C). In order to facilitate the horizontal and vertical alignment procedures, the X-ray beam may be shuttered or collimated to reduce the width of the X-ray beam to about a one-half inch transverse dimension.

The X-ray source 101 is now properly aligned to the isocenter 163. The X-ray source is locked in position.

Figure 17A:
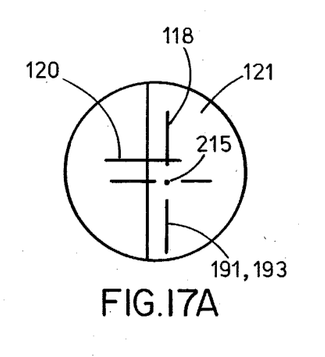
Figure 17B:
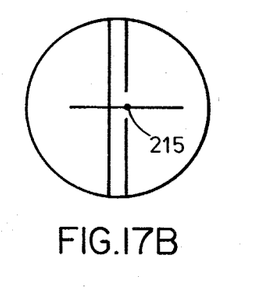
Figure 17C:
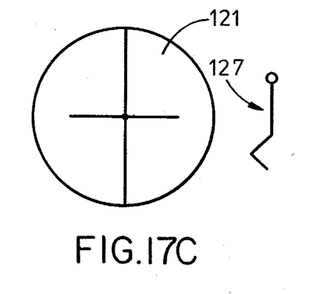

Aligning the Vascular Gantry System X-ray Image Intensifier to the Angleometer The final step in aligning the vascular gantry system 100 to the isocenter 63 of the frontal imaging system 50 is to align the X-ray image intensifier 103 of the vascular gantry to the isocenter. The first step is to adjust the distance between the focal spot of the X-ray source 101 to a known distance from the image input face of image intensifier 103. The procedure is basically the same as the procedure for aligning the X-ray source 101 with the isocenter and ball as was just described. FIG. 17 is analogous to FIG. 16 in the respect that FIG. 17(A) shows a possible image of the angleometer horizontal X-ray impervious lines 191 and 193 projected onto the non-aligned X-ray image intensifier input face 121. In FIG. 17, the X-ray impervious crossed lines 117 that are on input face 121 are shown. Referring to FIG. 17(A), to align the lines 117 and 119 on the image intensifier, the intensifier must be moved in both the horizontal and vertical directions. To make the horizontal correction, the mechanical connection between the X-ray image intensifier hanger intensifier 107 and the intensifier 103 is adjusted up or down or sideways as required. With proper alignment parallel to the Y axis, the image of the angleometer ball 215 and the horizontal X-ray impervious lines 191 and 193 on the target frame are as depicted in FIG. 17(B). The vertical correction is made by mechanically adjusting the extension or height of hanger 107 to the proper position. With the X-ray image intensifier 103 properly aligned, the image of the angleometer cross lines 191 and 193 and the ball appear on the television display screen as shown in FIG. 17(C).

The alignment procedures are now essentially complete. The vascular gantry system 100 is aligned to the angleometer which in turn is aligned to the frontal X-ray imaging system 50. The angleometer ball 215 is located at the isocenter 63 of the frontal imaging system and the vascular gantry system. Ball 215 is thus a point in space that does not move with respect to the central ray of X-ray beam 62 of the frontal imaging system or the central ray of beam 125 of the lateral or vascular gantry system. Consequently, for all combinations of frontal X-ray system and vascular gantry system angulations, the central ray of both X-ray beams will always pass through the point occupied by the ball which is the isocenter for both systems. With the patient's anatomy of interest placed at or near the isocenter, simultaneous posterior-anterior and lateral X-ray views may be taken. The views may be orthogonal to each other, as along the X and Z axes, or the views may be made at any angle within the permissible range of the two systems.

It should be noted that for establishing the isocenters of a frontal and a lateral X-ray system as just described, target 171 never had to be tilted out of level about axis 173 nor did support box 159 have to be rotated about vertical axis 157. Thus, except for use in connection with an angle calibration procedure which will be described next, the target frame 171 or a substantially solid block of plastic material having the x-impermeable crosshair lines 191, 200 and 193, 206 could be fixed directly on the base plate 151. Retaining the levelling screws 153 and the bubble level would also be desirable. Note, too, that the tiny X-ray impermeable ball 215 does not have to be exactly midway between the crosshair sets for the procedures thus far described, as long as the ball lies on a line on which the centers of the cross holes 211 and 213 lie.

Angular Calibration

The angleometer 150 is also useful for calibrating the vascular gantry system 100 for automatic or semiautomatic operation. Calibration is accomplished by recording the coordinates of the X-ray source 101 and X-ray image intensifier 103 at four angles within their angular ranges about each of two axes. With the vascular gantry system completely aligned to the isocenter 63 as illustrated in FIG. 17(C), the coordinates are entered into a microprocessor control which is not illustrated since by itself, it is not part of the invention claimed herein. The target frame 171 of angleometer 150 is first rotated 60° in one direction about axis 173. The 60° angle is measured by using reference line 219 on the tiltable target frame shown in FIG. 7 and reading off the angle from protractor 223 that is inscribed on front wall 167 of the angleometer box. The X-ray source 101 and X-ray image intensifier 103 are then rotated in their respective vertical planes, and the hangers 103 and 107 are correspondingly raised and lowered until the central X-ray beam 125 is aligned with the angleometer ball 215 and X-ray impermeable lines 191 and 193 are imaged in coincidence on the televison screen and they are coincident on the screen with X-ray impermeable strip 119 that is on the face 121 of intensifier 103. Thus, with the central beam 125 at a 60° angle relative to horizontal, the image of the ball 215 and the X-ray impermeable lines on the screen is as illustrated in FIG. 17(C). In that position, the Y coordinates of the vascular gantry system are entered into the memory of the microprocessor control system.

The calibration procedure is continued by rotating the angleometer box 159 about vertical axis 157 in the amount of 30°. Preferably, the angleometer box is rotated with the target frame 171 at the 60° attitude previously attained. Rotation about axis 157 is measured by using reference line 221 and protractor 225. The X-ray source and X-ray intensifier 103 are next rotated about their respective axes 113 and 114 and the corresponding carriages 67 and 69 are translated along track system 112 until the image of the angleometer on the X-ray detector is as illustrated in FIG. 17(C). The X-ray source 101 and X-ray image intensifier 103 coordinates are then entered into the microprocessor memory. The angleometer box is next rotated about vertical axis 157 to 30° on the opposite side of the zero position, and the procedure for aligning the X-ray source and intensifier to the new angleometer position is repeated. With the X-ray source and intensifier in proper aligned positions, the coordinates are entered into the memory in the microprocessor control. The control is capable of storing the entered data and using it to interpolate all intermediate rotational positions about horizontal axis 173 and vertical axis 157 to a high degree of accuracy.

Although a preferred embodiment of the invention has been described in detail, such description is intended to be illustrative rather than limiting, for the invention may be variously modified and its scope is to be limited only by interpretation of the claims which follow.

We claim:

1. A device for determining the location of the isocenter of an X-ray system comprising an X-ray source and an X-ray image receptor toward which the X-ray beam from the source is directed, and means supporting said source and receptor for making X-ray views at various angular aspects of a body supported on an X-ray transmissive table, the isocenter being defined as the point of intersection of the rotational axes of the supporting means and the central ray of the X-ray beam, said device comprising:
   a base plate,
   an X-ray permeable target mounted on said base plate and having side walls arranged in parallelism with each other, and crosshairs comprising a vertical X-ray impermeable line and an intersecting horizontal X-ray impermeable line inscribed on each side wall, the vertical lines lying in common vertical plane and the horizontal lines lying in a common horizontal plane, and
   a small X-ray impermeable ball secured in said target on a line extending between the nominal intersections of the crosshairs on each side wall.

2. The device according to claim 1 wherein said ball is located substantially mid-way between the points of intersection, respectively, of said X-ray impermeable lines on said target sides.

3. The device according to claim 1 including a level indicating means mounted to the device for determining if said horizontal lines are level when said device is mounted to said X-ray transmissive table.

4. The device according to claim 1 including leveling screws threaded into said base plate for bearing on said X-ray transmissive table, and a level indicating means mounted to said target referenced to said horizontal X-ray impermeable lines such that by adjusting said leveling screws while the device is on said X-ray table the impermeable lines can be made level.

5. The device according to claim 2 wherein said level indicating means is a bubble level.

6. The device as in claim 1 including means for supporting said target on said base plate for tilting about an axis parallel to and equidistant from said horizontal X-ray impermeable lines on said front and rear walls.

7. The device according to claim 1 wherein said target is supported for tilting on a horizontal axis and for rotating about a vertical axis that intersects the horizontal axis, including
   a base member and means mounting said member on said base plate for rotating on said vertical axis,
   a pair of spaced apart members projecting upwardly from said base member, at least one of said spaced apart members being a light-transparent plate to which the target tilting axis is perpendicular,
   a protractor circle having angle indicia affixed to said one plate concentric to said tilt axis and an opaque reference line on said target in parallelism with said transparent plate and in the same plane as said horizontal X-ray impermeable lines, such that the angle of tilt of said target can be measured by observing the angle indicia on the protractor that is crossed by said reference line.

8. The device as in claim 7 including a protractor circle concentric to said vertical axis and having angle indicia affixed to one of said base plate or said base member and a reference line affixed to the other of said plate or member to allow measurement of the angle of rotation of the base member about said vertical axis.

9. Apparatus for aligning a lateral X-ray imaging system to a frontal X-ray imaging system comprising:
   a base plate;
   box means mounted for rotation on the base plate about a substantially vertical axis;
   a target assembly mounted in the box means for rotation about a substantially horizontal axis intersecting the vertical axis, the target assembly comprising:
   an X-ray permeable target having spaced apart first and second walls disposed substantially parallel to the target assembly axis of rotation;
   Crosshairs on said walls defined by nominally vertical and horizontal intersecting X-ray impermeable lines, the vertical lines lying in a common plane and the horizontal lines lying in a common plane; and
   an X-ray impermeable ball mounted in the target at the intersection of the target assembly axis of rotation and the vertical axis so that rotation of the target assembly and box does not cause linear displacement of the ball.

10. The apparatus of claim 9 wherein a line connecting the intersections of the crosshairs is perpendicular to and intersects the target assembly axis of rotation.

11. The apparatus of claim 10 wherein the line connecting the intersections of the crosshairs intersects the ball.

12. The apparatus of claim 11 wherein the target first and second walls are substantially parallel and vertical.

13. The apparatus of claim 11 wherein the target defines a hole through the first and second walls at the intersection of the crosshairs.

14. The apparatus of claim 9 wherein the target assembly axis of rotation is approximately equidistant between the first and second opposed walls.

15. The apparatus of claim 11 further comprising means for measuring the angle of rotation of the target assembly about the horizontal axis of rotation and of the box means about the vertical axis of rotation.

16. The apparatus of claim 15 wherein the means for measuring the angle of rotation of the target assembly about the horizontal axis of rotation includes a reference line formed in the target and a cooperating protractor formed in the box means.

17. The apparatus of claim 16 including means for measuring the angle of rotation of the box means about the vertical axis comprising a line formed in the base plate and passing through the vertical axis and a cooperating protractor formed in the box means.

18. The apparatus of claim 9 further comprising level means for leveling the horizontal X-ray impermeable lines.

19. A method of determining the common isocenter of frontal X-ray imaging apparatus comprised of an L-arm rotatable about a vertical axis and a U-arm mounted to said L-arm for rotating about a horizontal axis and an X-ray source and an X-ray image receptor mounted to opposite legs of said U-arm and of lateral X-ray imaging apparatus comprised of an X-ray source and an X-ray image receptor mounted on laterally spaced apart vertically extending adjustable hangers, said source and receptor being mounted on said hangers for angulating about longitudinal axes, respectively, said method including the steps of:
(a) providing a horizontal and vertically adjustable patient support table having longitudinal and lateral axes corresponding to the patient's longitudinal and lateral axes, (b) providing an angleometer having a box rotatable about a vertical axis and a target rotatable in the box about a horizontal axis, the target having an X-ray imermeable ball mounted therein at the intersection of the horizontal and vertical axes of rotion, the target having crosshairs comprised of perpendicular vertical and horizontal X-ray impermeable lines mounted thereto on opposite sides of the ball and equidistant from the ball, said vertical and horizontal lines on each side lying in common vertical and horizontal planes, respectively;

(c) placing the angleometer on the patient support table at the approximated frontal imaging system isocenter;

(d) having the frontal imaging system U-arm in a vertical position;

(e) having intersecting longitudinally and laterally extending X-ray impermeable lines constituting crosshairs affixed on the image input plane of said image receptor;

(f) moving the patient support table horizontally to position the angleometer ball on the vertical axis and hence on the central ray of the X-ray beam of the frontal imaging system;

(g) manually adjusting the angleometer so that as viewed in an X-ray image of the angleometer the vertical crosshair lines on the target appear as dots coincident with the longitudinally extending line on the receptor and, hence aligned with the patient longitudinal axis;

(h) rotating the frontal imaging system U-arm to the horizontal position;

(i) moving the patient support table vertically as required until an X-ray view reveals that the angleometer ball is at the elevation of the frontal imaging system isocenter;

(j) rotating the lateral imaging system X-ray source so that the central ray of the beam thereof is horizontal;

(k) rotating the lateral imaging system X-ray source so that the central ray of the beam thereof is in a vertical plane lateral to the patient;

(1) linearly adjusting the X-ray source horizontally so that the central ray of the beam thereof intersects a vertical line passing through the angleometer ball and both X-ray impermeable vertical lines on the target;

(m) linearly adjusting the X-ray source vertically so that the central ray of the beam thereof intersects the angleometer ball and both vertical lines;

(n) rotating the lateral X-ray receptor to a horizontal attitude;

(o) linearly adjusting the X-ray receptor horizontally so that the central ray of the beam from the X-ray source intersects a vertical line passing through the center of the X-ray receptor image input plane; and (p) linearly adjusting the X-ray image receptor vertically so that the X-ray source central ray intersects the center of the X-ray receptor image input plane.

20. The alignment method of claim 19 further including a method of calibrating the lateral imaging system comprising the additional steps of:

(a) entering the coordinate data of the lateral system X-ray source and X-ray image receptor to a microprocessor control;

(b) rotating the angleometer target a predetermined amount about the horizontal axis of rotation;

(c) rotating and translating the X-ray source and X-ray image receptor correspondingly so that the central ray of the X-ray beam from the source intersects the angleometer ball and is aligned with the angleometer cross strips and strikes the center of the X-ray image receptor image input face;

(d) entering the coordinate data of the X-ray source and X-ray image receptor to the microprocessor control;

(e) rotating the angleometer box a predetermined amount about the vertical axis;

(f) rotating and translating the X-ray source and X-ray image receptor correspondingly so that the central ray of the beam from the X-ray source intersects the angleometer ball and is aligned with the angleometer X-ray impermeable lines and strikes the center of the X-ray detector screen;

(g) entering the coordinate data of the X-ray source and X-ray image receptor to the microprocessor control;

(h) rotating the angleometer box to a second predetermined angle about the vertical axis;

(i) rotating and translating the X-ray source and X-ray detector correspondingly so that the central ray from the X-ray source intersects the angleometer ball and is aligned with the angleometer X-ray impermeable lines and strikes the center of the X-ray image receptor image input face; and (j) entering the coordinate date of the X-ray source and X-ray image receptor to the microprocessor control.

* * * * *